United States Patent [19]

Jelsma et al.

[11] Patent Number: 4,566,445

[45] Date of Patent: Jan. 28, 1986

[54] STRETCHER FOR PERSONS WITH SPINAL INJURIES

[76] Inventors: Richard K. Jelsma, 102 Wampum Rd., Louisville, Ky. 40207; Charles H. Choi, 5279 Kelvin Ave., Apartment 11, Canoga Park, Calif. 91306; Thomas G. Hynes, 20440 Celtic, Chatsworth, Calif. 91311

[21] Appl. No.: 518,352

[22] Filed: Jul. 29, 1983

[51] Int. Cl.[4] .......................... A61F 5/00; A61G 1/00; A61G 13/00; A47C 19/16

[52] U.S. Cl. .......................................... 128/70; 5/82 R; 5/111; 269/322

[58] Field of Search ............ 128/70; 428/319.3, 319.7; 5/82, 82 R, 89, 111, 114; 269/322, 323, 328

[56] References Cited

U.S. PATENT DOCUMENTS

| | | | |
|---|---|---|---|
| 879,335 | 2/1908 | Southmayd | 5/82 |
| 1,586,355 | 5/1926 | DeFranco | 5/111 |
| 2,753,233 | 7/1956 | Rock | 269/328 |
| 2,926,660 | 3/1960 | Thompson | 269/322 |
| 2,947,007 | 8/1960 | Oades | 5/82 |
| 3,139,883 | 7/1964 | Collins | 5/82 X |
| 3,648,305 | 3/1972 | Ersek | 5/82 X |
| 3,886,606 | 6/1975 | Bradford | 5/82 |
| 3,947,686 | 3/1976 | Cooper et al. | 269/322 X |
| 4,024,861 | 5/1977 | Vincent | 128/134 X |
| 4,205,111 | 5/1980 | Pip et al. | 428/319.7 X |
| 4,484,571 | 11/1984 | Velazquez | 128/134 |

*Primary Examiner*—Richard J. Apley
*Assistant Examiner*—Alan W. Cannon
*Attorney, Agent, or Firm*—Sheldon & Mak

[57] ABSTRACT

A stretcher for traumatized patients comprises a rigid board having a central core of polyimide foam and a skin of graphite reinforced expoxy; this board is exceptionally radiolucent. The board has built in handles for transporting the patient, straps for holding a patient on the board, and means for applying traction to a patient. The stretcher is designed for transporting the patient and applying a variety of diagnostic tests to the patient, including computer aided tomography scanning, without removing the patient from the stretcher. It also facilitates efforts to make a closed reduction of a cervical fracture with fluoroscopic monitoring.

16 Claims, 11 Drawing Figures

FIG. 9
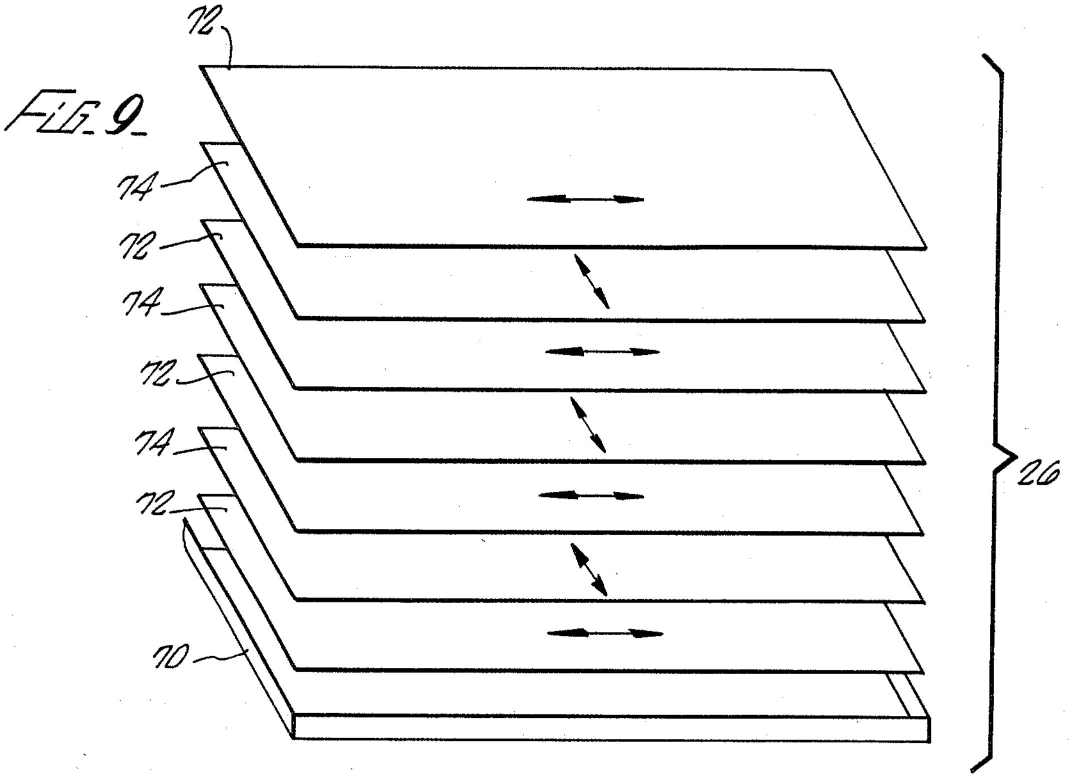
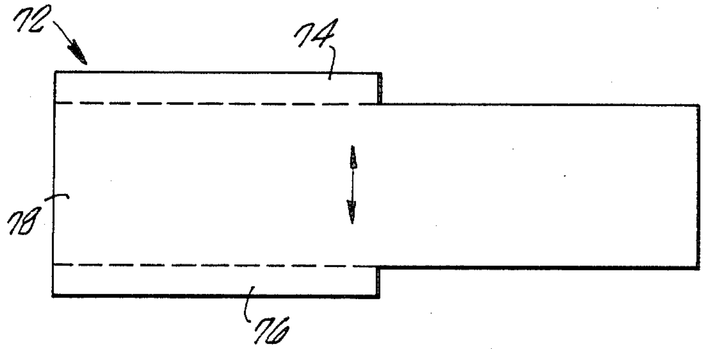
FIG. 11
FIG. 8
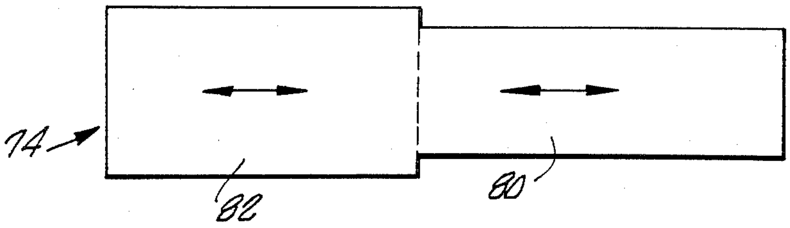
FIG. 10
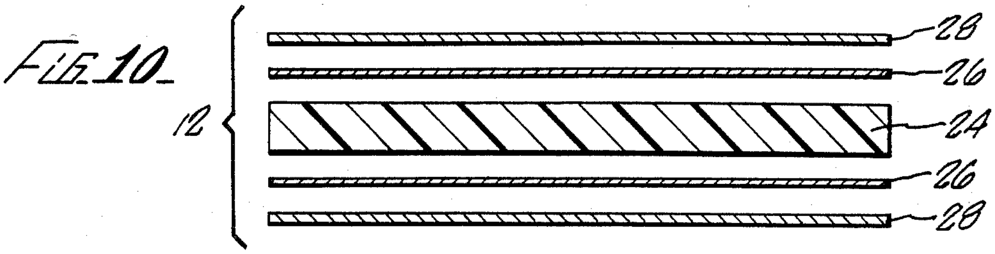

STRETCHER FOR PERSONS WITH SPINAL INJURIES

BACKGROUND

The present invention is directed to a stretcher particularly useful for persons with spinal injuries.

It is very important with persons with spinal injuries to maintain such persons immobile to minimize damage to the spine and to avoid further trauma. A patient with spinal damage can be subjected to a variety of diagnostic tests including plain X-rays, computer aided tomography (referred to as CT below), standard myelograhy, and CT myelography. During myelography, often a patient is not maintained horizontal, but needs to be raised up to 60° relative to the horizontal.

Besides these diagnostic techniques, manipulation of a patient with a spinal fracture can be done. For example, a closed reduction of a spinal fracture can be effected where the patient is held on a board with traction applied while the patient is in an X-ray machine so that the effect of the manipulation on the fracture can be monitored.

When making the radiographic evaluation of a patient with a spinal fracture, it is often necessary to move the patient from stretchers to dollies to other flat surfaces, depending upon the diagnostic test the patient is undergoing. This is undesirable because in some circumstances this movement can cause additional trauma to the spine and spinal cord. Application of cervical traction is often required to make these diagnostic tests properly, and also to reduce a fracture, and this requires additional cubmersome equipment which is difficult to acquire and set up at the place it is needed.

Thus, there is a need for a stretcher that can hold a patient with a spinal injury, which is sufficiently radiolucent to allow high quality X-ray and CT studies even though the patient remains on the stretcher when they are made, and which has an attached traction device.

SUMMARY

The present invention is directed to an article that satisfies these requirements. The article includes an elongated rigid board that is formed as a laminate of a central core of foam, preferably rigid polyimide foam, and an outer skin of graphite reinforced epoxy. This board has an aluminum equivalency of less than 1 mm and a CT number of less than 50 so that it can be used in X-ray machines and CT scanners. The board is provided with a plurality of straps for holding the patient to the board with the patient's spine immobilized. Preferably at least a portion of the straps include handles so that the board can be carried easily.

For patient comfort, preferably there is a cushion pad on the top surface of the board. The pad and board together preferably have an aluminum equivalency of less than 1 mm.

Preferably the torso portion of the board is sufficiently narrow that it can be inserted into a CT scanner, while the leg portion of the board is wider for additional support of the patient. Generally the leg portion is at least three inches wider than the torso portion. Both the leg and torso portions are at least 2 feet long.

The board is sufficient rigid that it can hold a 250 pound patient with substantially no flexing.

Because the surface on which the board rests in many scanners is curved, preferably the underside of the board is provided with feet or stops so that the board can sit securely on a concave surface. Also, the board rests securely on flat X-ray tops.

Preferably means for applying traction to the patient is mounted at the head of the board.

Once a patient is placed on the stretcher, it is not necessary to move him off it at any time during the complete radiographic evaluation of a spinal fracture or the closed reduction of a cervical fracture. The patient can remain on the stretcher for plain X-rays, myelograms and CT scans because of its low aluminum equivalency and low CT number. A patient resting on this novel stretcher can undergo modern diagnostic techniques and treatments more effectively and with less risk of additional trauma to his spine than with prior art stretchers.

DRAWINGS

These and other features, aspects and advantages of the present invention will become better understood with reference to the following description, appended claims, and accompanying drawings where:

FIGS. 7-11 show different steps used to assemble a board according to the present invention.

DESCRIPTION

Figures 1, 2, 3:
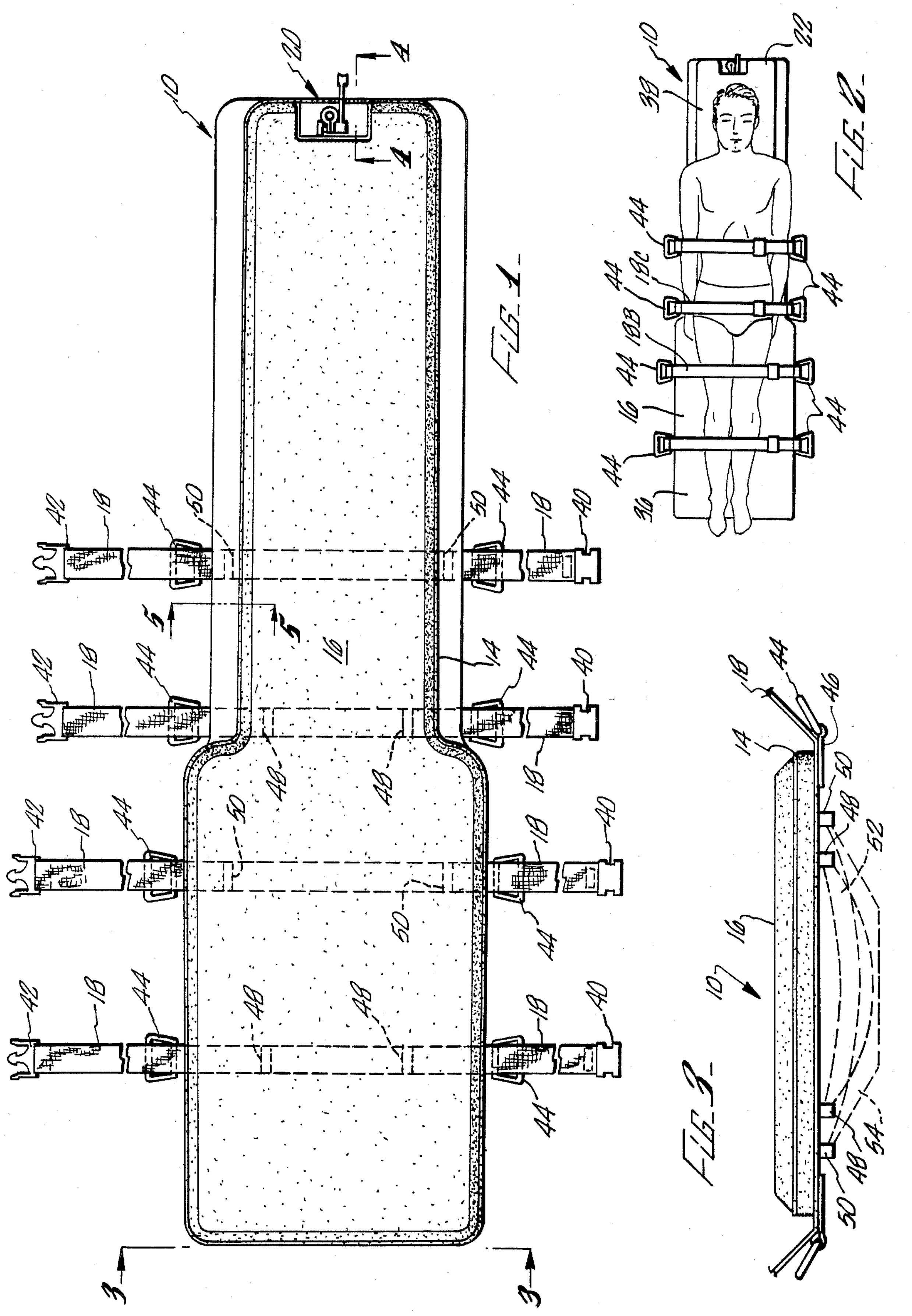
FIG. 1 is a plan view of a stretcher according to the present invention with a patient strapped thereon.
FIG. 2 is a plan view of the stretcher of FIG. 1 without a patient thereon.
FIG. 3 is an elevation view of the stretcher of FIG. 1 taken along line 3—3 of FIG. 2 from the foot of the stretcher.
Figure 6:
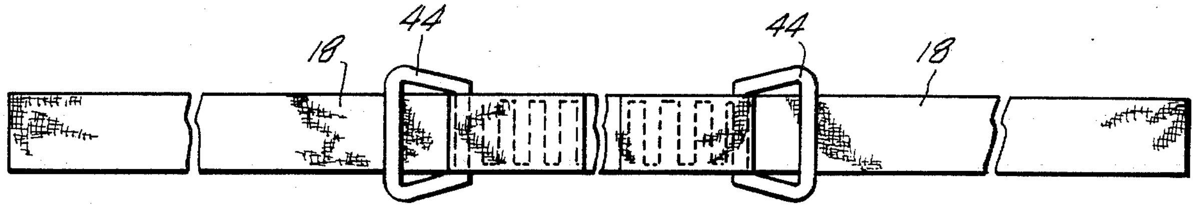
FIG. 6 is a plan view of a strap used with the board of FIG. 2.

A stretcher 10 according to the present invention, as shown in FIGS. 1-5 is particularly adapted for a patient 12 having suffered trauma to his spine. The stretcher 10 comprises a rigid board 14, a pad 16 on top of the board, a plurality of straps 18, and a traction device 20 at the head end 22 of the stretcher.

Figure 5:
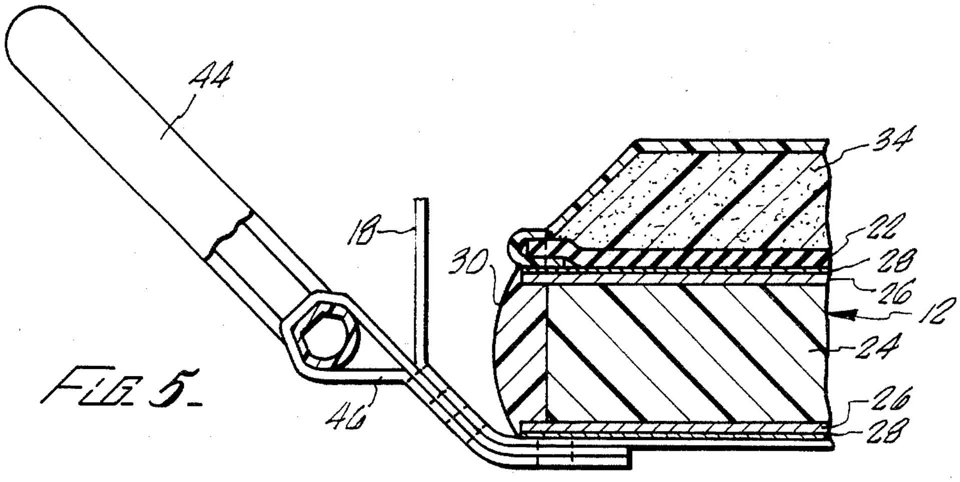
FIG. 5 is a sectional view of one of the side edges of the board of FIG. 2 taken along line 5—5 of FIG. 2.
Figure 4:
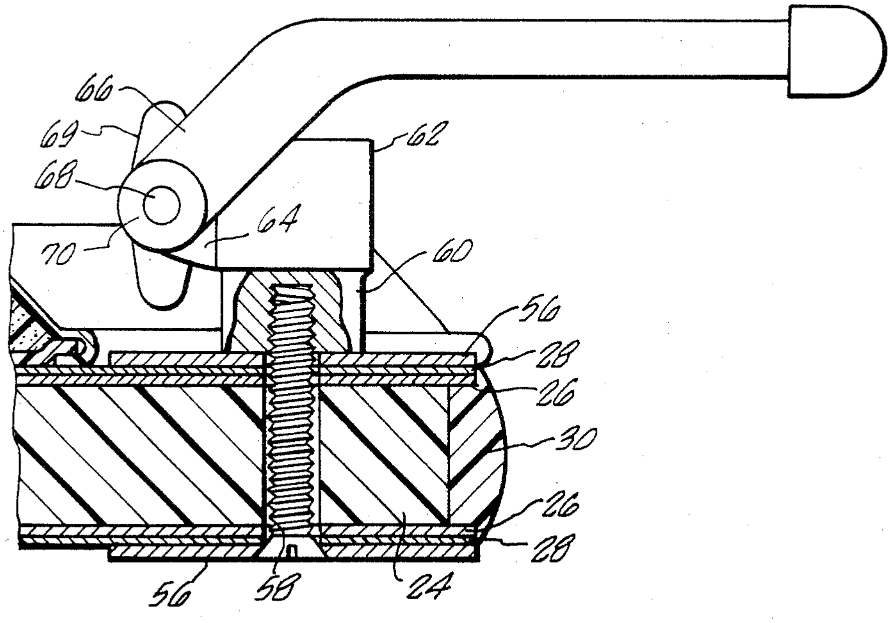
FIG. 4 is a sectional view of the device for applying traction of the board of FIG. 2 taken along line 4—4 of FIG. 2.

With reference to FIGS. 5 and 10, the board 14 comprises a laminate having a central core of foam 24 and an outer skin 26 of graphite reinforced epoxy material, i.e., the foam is sandwiched between two layers or laminates 26 of graphite reinforced epoxy material. For texture and appearance, both layers or skin 26 of epoxy can be covered with textured decorative paper 28. Preferably the foam 24 is a rigid foam, and more preferably polyimide foam.

The paper 28, graphite/epoxy skin 26, and polyimide foam 24 can be laminated together under pressure and elevated temperature as the epoxy resin is cured.

A suitable "prepreg" graphite reinforced epoxy resin is commercially available from Fiberite of Winonia, Minn. under the tradename HYE 1048 A1E. Suitable polyimide foam is available from Cyro Industries of Stanford, Conn. under the tradename Rohacell 71 WF.

This board 12 has many advantages for use in a stretcher. It is lightweight, has a low aluminum equivalency and a low CT number. This means that it is useable in both conventional X-ray machines and CT scanners without introducing artifacts. Aluminum equivalency values presented herein are those determined in accordance with Title 21, Section 1020.30n of the Code of Federal Regulations and are determined by X-ray measurements made at 100 kvp with a minimum first half-value layer of 2.7 mm aluminum.

The aluminum equivalency of a board according to the present invention, made of polyimide foam and graphite reinforced epoxy resin, was less than 0.5 mm. The federal standard for a movable table-top is 1.5 mm.

The stretcher 10 and board 14 are rigid. A board 14 0.775 inch thick comprising foam about 0.695 inch thick and each graphite layer about 0.04 inch thick can easily serve as a stretcher for a 250 pound patient.

The term "CT" value refers to the number measured when comparing the absorption and refraction of X-rays in various materials when compared to a known substance, air or water. All of the components of the stretcher 10, other than the metallic traction device 20, have a CT value less than 50.

A particular advanatage of using a polyimide core is that such a core can be subject to high temperatures and pressures to allow lamination with the epoxy resin/graphite layers while the epoxy resin is cured. Other materials, such as polyurethane foam, would collapse under the pressures and temperatures used for curing the graphite reinforced epoxy, and most would have a higher aluminum equivalence.

However, the present invention is not limited to the use of polyimide foam cores; another material that can be used is Nomex (DuPont Trademark) honeycomb core.

A board with a polyimide core and graphite reinforced epoxy skin is sufficiently rigid that it can support a 250 pound patient when the board is lifted at each end with less than ½ inch maximum deflection. Further, the board is sufficiently rigid that when the stretcher is lifted at each end with a 300 pound weight at its center, there is less than one inch deflection at the middle of the stretcher. When the board is picked up with handles 44, there is literally no deflection.

The entire peripheral edge of the board 14 is covered with an extruded bumper 30 made of polyurethane that is located between the graphite/epoxy skins 26 and bonded to the polyimide foam core 24 with an epoxy adhesive.

The pad 16 is included in the stretcher 10 so that the patient lays on a comfortable surface. The pad 16 is generally the same shape as the board 14, but is smaller in all directions so that the edges of the pad 16 are not exposed.

As shown in FIG. 5, the pad 16 comprises a bottom layer 32 of non-skid rubber, and a top layer 34 of polyester sponge. The top of the sponge and the edges of both the sponge layer 34 and rubber layer 32 are covered with a durable vinyl material 35 such as Naugahyde TM. A suitable pad 16 can be obtained fron Contour Fabricators, Incorporated, located in Grand Blanc, Mich. A pad about one inch thick has a low aluminum equivalence of about 0.6 mm of aluminum and a low CT number of less than 50.

The stetcher 10 has a leg portion 36 and a torso portion 38. The torso portion 38 is narrower than the leg portion 36 and generally at least about three inches narrower. Preferably the torso portion is sufficiently narrow to pass into the gantry of a CT scanner. The leg portion is wider to support the pelvis, the forearms, and hands. Preferably the leg portion is sufficiently narrow to fit between the clamps which secure the feet to commonly used fluoroscopic tables; if the stretcher is too wide it does not fit between the clamps and cannot rest on the foot plate.

Preferably the torso section is more than 15 inches wide because anything less narrow would not function well as a stretcher and would be undesirable with patients with multiple injuries. Preferably the torso section is about 18 inches wide to fit through the gantry of commonly used scanners.

Preferably the torso section is at least 42 inches long because this permits the lowest lumbar vertebrae, even in very tall patients, to pass into a CT scanner gantry.

Preferably the leg section is at least 38 inches long so the stretcher is long enough to support the entire patient, injuries of the lower spine, pelvis, or legs are immobilized better when the legs are supported. Preferably the leg section is less than 22 inches wide to fit between the clamps which secure the foot plate to commonly used fluoroscopic tables.

The straps 18 are bonded to the underside of the board 14 with an adhesive such as polyurethane adhesive. A satisfactory adhesive is made by Hexcel of Chatsworth, Calif. and sold under the tradename Uralite XW20-42-4. The straps are provided with male 40 and female 42 buckles with the location of the male buckle 40 on the straps being adjustable. Four straps are provided for securing the patient across the shins, the thighs, the hips, and the torso. The straps can be made of polyester fiber or nylon and the buckles of a strong polymeric material.

The stretcher 10 is provided with eight handles 44. The handles 44 are secured to webbing 46 that is sewn to the straps 18. Two handles are attached to each of the four straps on opposite sides of the stretcher. The webbing 46 can be made of a strong, flexible fabric material such as polyester or nylon and the handles 44 can be formed from a strong polymeric material such as nylon, ABS, or high impact polystyrene.

The underside of the board 14 is provided with eight feet or stops, four feet 48 laterally inwardly and four feet 50 laterally outwardly. The stops are provided in pairs along the lower portion of the board 14. Preferably they are made from a tough polymeric material having a relatively low aluminum equivalency such as cast polyurethane.

These stops allow the board to sit on a concave surface even though the bottom of the board is flat. For example, with reference to FIG. 3, the four inner stops 48 are positioned to hug the cradle 52 of a scanner having a low radius of curvature such as the General Electric model 8800 CT scanner, while the four outer stops 50 are positioned to hug the cradle 54 of a scanner having a larger radius of curvature such as the General Electric model 9800 CT scanner. The stops can be located wherever desired to accommodate the curvature of the scanner with which the board is to be used.

The only metallic part of the stretcher 10 is the traction device 20. The traction device comprises a pair of aluminum support plates 56, one on the top and one on the bottom of the rigid board 14, and held to the board by a screw 58 and epoxy adhesive. Mounted on the screw 58 on top of the upper support plate is a base 60 on which there is rotatably mounted a collar 62. The collar 62 includes an ear 64 on which is pivotally mounted a traction bar 66, held on the ear with a pivot pin 68. A handle 69 with a sunburst clamp 70 holds the traction bar 66 in position. The traction bar 66 is centrally located at the head of the stretcher.

The traction device is an adaptation of a Gardener skull clamp adaptor made by Mayfield and available from Codman and Shurtleff, Inc. of Randolf, Mass.

This stretcher 10 has significant advantages, including the following:

1. It is exceptionally radiolucent so that good quality X-ray and CT images of the entire spine can be obtained without taking the patient off it.

2. It is large, strong and stiff enough to serve as a stretcher and to allow lifting at the ends with even a 250 pound patient lying on the board, even though it is light-weight, less than 25 pounds.

3. It is narrow enough to fit through the aperture of commonly used CT scanners along the entire length of the spine.

4. It includes a cervical traction device which can accommodate up to 80 pounds of traction at variable angles.

5. It is stable when secured to a fluoroscopy table even when tilted upwardly during myelography. Paralyzed patients have been elevated as high as 60 degrees in order to return the contrast medium to the lower spinal canal following completion of myelographic studies, when the patient's feet and the lower edge of the board were rested against the foot plate of the fluorscopic table and a retractable binder was tightened over the patient's knees and secured to the fluoroscopic table.

6. A paralyzed patient can be securely attached to the stretcher by means of the straps.

7. The stretcher is padded to protect a paralyzed against the development of decubiti.

8. Because of the feet, the stretcher fits onto a concave CT cradle securely to reduce the chance of movement of the stretcher in relation to the cradle. In addition, the stretcher sits securely on flat tables including X-ray tables.

9. It has excellent hand grips to permit lifting from the sides.

In short, once a patient is placed on the stretcher 10 it is possible to safely conduct a complete radiographic evaluation of the spine and spinal cord.

These and other features of the present invention will become better understood from the following example.

EXAMPLE

A stretcher according to the present invention had a total thickness of about 1.8 inches, with the pad 1 inch thick and the board 0.8 inch thick. The stretcher was 80 inches in length, 18 inches wide in the torso portion, and 21½ inches wide in the leg portion. The torso portion was 42 inches long and the leg portion was 38 inches long. The pad was only 14 inches wide in the leg portion to minimize the artifacts produced by the pad in an X-ray device. The board included straps, handles, and a traction device as shown in FIG. 1.

With reference to FIGS. 7–11, the board 14 was formed from laminates 26 made from seven layers of graphite reinforced resin placed on a lay up table 70. The alternating layers were oriented 90 degrees relative to each other. The bottom, third, fifth and top layers 72 were oriented in one direction while the second, fourth and sixth layers 74 were oriented 90 degrees relative to layers 72. The direction of a layer is determined by the direction in which the graphite fibers are layed in the epoxy matrix. The material for layers 72 and 74 was graphite reinforced epoxy resin prepreg obtained from Fiberite, Catalog No. HYE 1048 A1E.

With reference to FIG. 7, the layers 72 were formed by butt splicing two segments 76 to the sides of elongated segments 78.

With reference to FIG. 8, the layers 74 were made by butt splicing a narrower segment 80 to a broader segment 82.

Figure 11:
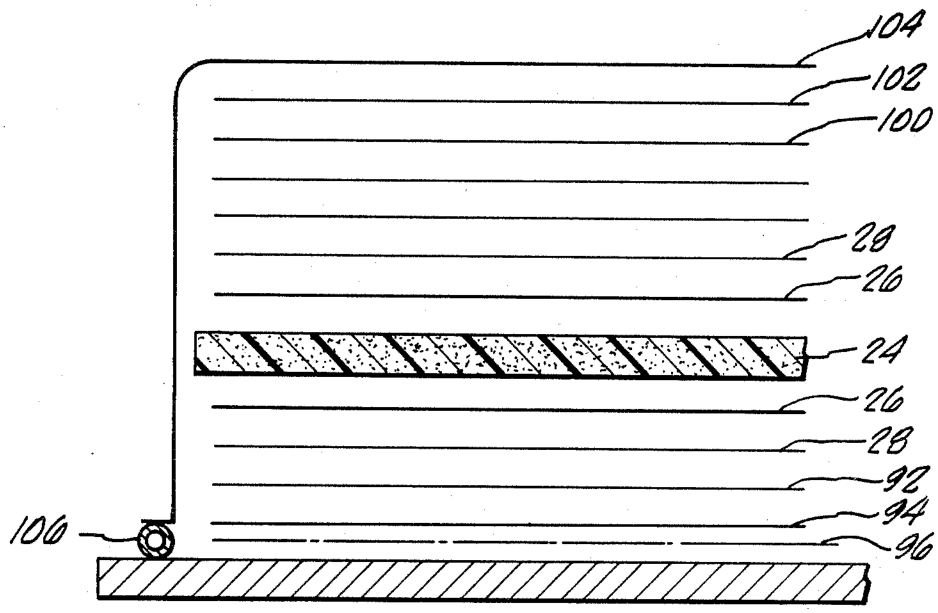

With reference to FIG. 11, a polyimide foam core 24 was sandwiched between two of these graphite epoxy preplies 26. The polyimide foam was Catalog Part No. 71-WF from Cyro Industries of Clifton, N.J. Then on top of both of the preplies, there was placed a layer of paper. The paper used was Moroccan leather available from Carolina Gravure of Lexington, S.C., Catalog No. C-65-349-XL. It was 65 pound paper and had a thickness of 4 mils. Both sides of this assembly were covered with one ply of mylar TM 92, which is a polyester resin, one ply of remay TM, which is a breather. This assembly was placed on an aluminum caul plate with a mold release agent therebetween. An aluminum caul plate 100, 0.125 inch thick, was placed on top of the assembly with a two ply remay breather 102 on top of the caul plate. The entire assembly was covered with a nylon vacuum bag 104 provided with a vacuum sealant 106.

To cure the epoxy/graphite and to achieve the necessary lamination, the following cure cycle was used.

The vacuum bagged parts were run under full vacuum for at least 30 minutes at a vacuum of 25 inches of mercury with a maximum leak rate of 1 inch per minute. The parts were then heated by raising the temperature to 175° F.±5° F. at a rate of 2°–5° F. per minute. When the part temperature reached 175° F., the pressure was set at 50 psi. When 50 psi was reached, it was held there for 15 minutes. Then the temperature was raised to 250° F.±5° F. at 2°–5° F. increase per minute. After the part reached a temperature of 250° F., it was held there for 1½ hours. The temperature was then quckly decreased. The pressure was released when the part temperature was below 175° F. The total cycle time was about 3 hours.

The thickness of the various layers are not shown to scale in the figures.

Although the present invention has been described in considerable detail with reference to certain preferred versions, other versions are possible. For example, the traction bar 62 need not rotate on the base 60. Therefore, the spirit and scope of the appended claims should not necessarily be limited to the description of the preferred versions contained herein.

What is claimed is:

1. A rigid, portable, radiolucent stretcher suitable for transporting and supporting a traumatized patient and suitable for radiographic examination of a traumatized patient, the stretcher comprising:

(a) an elongated rigid board having a top surface, a substantially flat bottom surface, a torso portion, and a leg portion, the board having a longitudinal centerline and comprising a laminate having a central core of polyimide foam and a skin of graphite reinforced epoxy material, the board having an aluminum equivalency of less than 1 mm;

(b) adjustable straps for holding a patient on the board;

(c) a cushion pad on the top surface of the board, the aluminum equivalency of the pad and board together being less than 1.5 mm;

(d) means for applying traction to a patient and means for securing the traction applying means to the board at the head thereof;

(e) a first set of stops and a second set of stops on the bottom surface of the board, each stop of the first set of stops being separated a first distance from the centerline of the board so the stretcher can sit securely on a first concave surface, each stop of the second set of stops being positioned a second distance from the longitudinal centerline of the board so that the stretcher can sit securely on a second concave surface, the first distance being different from the second distance, and the curvature of the first concave surface being different from the curvature of the second concave surface; and (f) means for lifting the stretcher.

2. The stretcher of claim 1 in which the lifting means are provided by at least a portion of the straps having handles.

3. The stretcher of claim 1 in which the board is narrower at the torso portion than at the leg portion.

4. An elongated rigid board for supporting a traumatized patient, the board having a torso section and a leg section, each at least two feet long, the torso section being at least 3 inches narrower than the leg section, the board having a top surface and a substantially flat bottom surface, the board having a longitudinal centerline, the bottom surface of the board having a first set of stops and a second set of stops thereon, each stop of the first set of stops being positioned a first distance from the longitudinal centerline of the board so that the board can sit securely on a first concave surface, each stop of the second set of stops being positioned a second distance from the longitudinal centerline of the board so that the board can sit securely on a second concave surface, the first distance being different from the second distance, the curvature of the first concave surface being different from the curvature of the second concave surface.

5. The board of claim 4 comprising a plurality of straps secured to the board for securely holding a patient on the board.

6. The board of claim 5 in which at least a portion of the straps have handles.

7. The article of claim 5 comprising four straps for holding a patient at the shins, thighs, pelvis and torso.

8. The board of claim 4 including means for applying traction to the patient, the applying means being mounted at the head of the board.

9. A portable stretcher comprising:

(a) an elongated rigid board having a top surface, a flat bottom surface, a torso portion, and a leg portion, the board having a longitudinal centerline and comprising a laminate having a central core of rigid polyimide foam and a skin of graphite reinforced epoxy material, the board having an aluminum equivalency of less than 1 mm, the leg portion being at least 3 inches wider than the torso portion, and both the leg portion and the torso portion each being at least 2 feet long;

(b) mounted at the head of the board, means for applying traction to a patient on the board;

(c) a first set of stops and a second set of stops on the bottom surface of the board, each stop of the first set of stops being positioned a first distance from the centerline of the board so the stretcher can sit securely on a first concave surface, each stop of the second set of stops being positioned a second distance from the longitudinal centerline of the board so that the stretcher can set securely on a second concave surface, the first distance being different from the second distance and the curvature of the first concave surface being different from the curvature of the second concave surface; and (d) a plurality of straps secured to the board for securely holding a patient on the board, at least a portion of the straps having handles.

10. A rigid, portable, radiolucent stretcher suitable for transporting and holding a traumatized patient and suitable for radiographic examination of a traumatized patient, the stretcher comprising:

(a) an elongated rigid board having a top surface, a bottom surface, a torso portion, and a leg portion, the board being narrower at the torso portion than at the leg portion, the board having a longitudinal centerline and comprising a laminate having a central core of foam and a skin, the board being sufficiently rigid when that the stretcher is lifted at its end with a 250 pound patient on the stretcher, the maximum deflection of the board is less than ½ inch, the board having an aluminum equivalency of less than 1 mm;

(b) means for holding a patient on the board; and (c) a first of stops and a second set of stops on the bottom surface of the board, each stop of the first set of stops being positioned a first distance from the longitudinal centerline of the board so that the stretcher can sit securely on a first concave surface, each stop of the second set of stops being positioned a second distance from the longitudinal centerline of the board so that the stretcher can set securely on a second concave surface, the first distance being different than the second distance and the curvature of the first concave surface being different from the curvature of the second concave surface.

11. The article of claim 10 including a cushion pad on the top surface of the board.

12. An article suitable for holding a traumatized patient rigidly and suitable for radiographic examination of a traumatized patient comprising:

(a) an elongated rigid board having a top surface and a substantially flat bottom surface and a longitudinal centerline;

(b) means for securely holding a patient on the board; and (c) a first set of stops and a second set of stops on the bottom surface of the board, each stop of the first set of stops being positioned a first distance from the longitudinal centerline of the board so that the stretcher can sit securely on a first concave surface, each stop of the second set of stops being positioned a second distance from the longitudinal centerline of the board so that the stretcher can sit securely on a second concave surface, the first distance being different than the second distance and the curvature of the first concave surface being different from the curvature of the second concave surface.

13. The stretcher of claim 1 in which the board is sufficiently rigid that when the stretcher is lifted at its ends with a 250 pound patient on the stretcher, the maximum deflection of the board is less than ½ inch.

14. The stretcher of claim 1 wherein the board has an aluminum equivalency of less than 0.5 mm.

15. The stretcher of claim 3 in which the board is at least 3 inches narrower at the torso portion than at the leg portion.

16. The stretcher of claim 15 in which the torso portion and the leg portion are each at least 2 feet long.

* * * * *